US006475362B1

(12) United States Patent
Gorfinkel et al.

(10) Patent No.: US 6,475,362 B1
(45) Date of Patent: Nov. 5, 2002

(54) METHOD AND APPARATUS FOR COMPRESSION OF DNA SAMPLES FOR DNA SEQUENCING

(75) Inventors: Vera Gorfinkel, Stony Brook; Mikhail Gouzman, Lake Grove; Luryi Serge, Old Field, all of NY (US)

(73) Assignee: Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 09/454,094

(22) Filed: Dec. 3, 1999

Related U.S. Application Data

(60) Provisional application No. 60/110,720, filed on Dec. 3, 1998.

(51) Int. Cl.⁷ .............................................. G01N 27/26
(52) U.S. Cl. ...................................... 204/451; 204/453
(58) Field of Search ................................ 204/451, 601, 204/453, 455, 604, 605

(56) References Cited

U.S. PATENT DOCUMENTS 3,720,593 A * 3/1973 Juhos ......................... 204/553

FOREIGN PATENT DOCUMENTS

JP              40572178 A    *   3/1993

OTHER PUBLICATIONS

JAPIO abstract of Kanbara (JP40572178A).*

* cited by examiner

Primary Examiner—Jill Warden
Assistant Examiner—Alex Noguerola
(74) Attorney, Agent, or Firm—F. Chau & Associates LLP

(57) ABSTRACT

A novel method of spatial compression of a DNA sample inside the capillary for the gel capillary electrophoresis and an article for operating the method are disclosed. In this method, after the electrokinetic injection, the sample is compressed using the reverse electric field. A special DNA barrier material is used to contain the sample in the capillary. We expect that this Electro Static Compression (ESC) can increase the DNA concentration in the capillary by orders of magnitude. In the proposed method and article the injection and compression of the DNA sample are followed by subsequent electrophoretic separation in any kind of sequencing container (for instance glass capillary). The use of the ESC method will allow the increase of the length and the quality of the read, as well as reduction of the DNA consumption. ESC method will also permit the use of low power illumination sources including miniature and inexpensive light emitting diodes (LED) instead of the Ar-ion laser for exciting fluorescent labels in 4-color DNA sequencing.

11 Claims, 3 Drawing Sheets

US 6,475,362 B1

METHOD AND APPARATUS FOR COMPRESSION OF DNA SAMPLES FOR DNA SEQUENCING

CROSS-REFERENCE TO RELATED APPLICATIONS

This application claims priority to Provisional Application Serial No. 60/110,720 filed Dec. 3, 1998 and incorporated herein by reference.

TECHNICAL FIELD

The present invention relates to a method and apparatus for compressing DNA samples for DNA sequencing.

BACKGROUND

The aim of the proposed method for in-capillary densification of the DNA analyte is to obtain a very sharp compressed DNA samples which can be separated in shorter separation times and experience less diffusion. Therefore, a need exist for a new technique which has higher sensitivity and better resolution than the conventional state-of-the-art techniques. This will moreover allow us to extend the range of the separation to larger DNA fragments.

SUMMARY

Notably, the new technique will be less expensive. Indeed, since in the ESC method the injected DNA sample will be compressed into a narrow zone, the injection time is not limited to rather short few seconds interval, but can be extended to several minutes. This means that the method will allow to use low-concentration DNA samples and minimize the waste of costly DNA material. The intensity of the excited fluorescent radiation from the condensed DNA sample will be strongly enhanced. This in turn will allow us to use low-intensity illumination sources in the detection module of our DNA sequencing instrument which will reduce the cost and expand the versatility of the sequencing instruments.

In the present section we provide a short review of the state-of-the-art of densification techniques in the DNA capillary electrophoresis (CE) of and discuss our motivation to develop a new method, for the DNA sequencing industry.

DETAILED DESCRIPTION OF PREFERRED EMBODIMENTS

Figure 1:
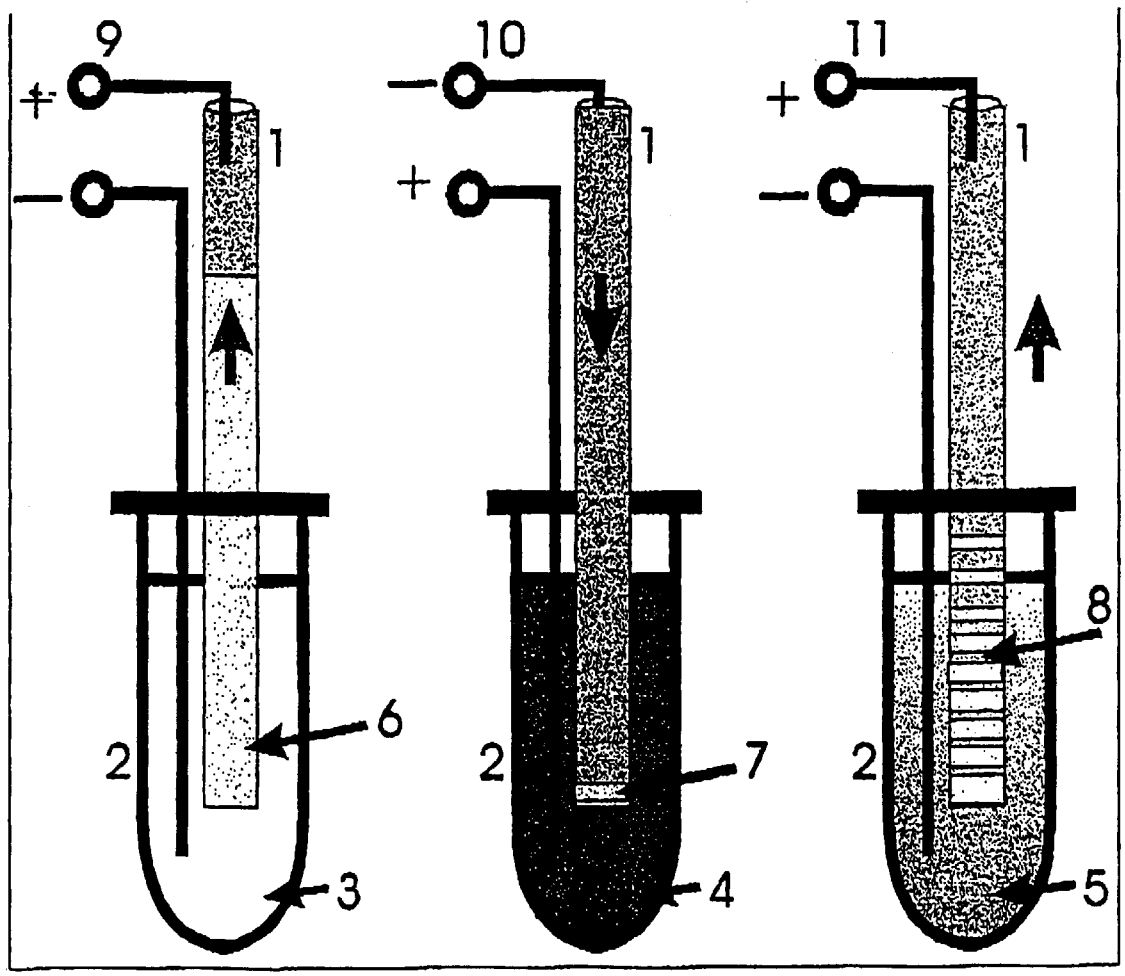
FIG. 1 is depicts a three-tube electroinjection in accordance with the present invention.

In capillary electrophoresis, a sample is usually introduced into the capillary by electrokinetic injection. This method has the advantage of a built-in sample compression mechanism. The mobility of injected DNA fragments is greatly reduced when they enter the capillary, due to a steep gradient in the strength of the electric fields at the inlet of the capillary [Wolf 95]. In gel CE, the mobility is additionally reduced by a confining effect of the gel matrix. Because of this deceleration, the crowding, or stacking, of the injected species occurs in the capillary near its inlet. This stacking effect usually increases the sample concentration of charged moieties by about an order of magnitude.

Unfortunately, the stacking phenomenon is greatly influenced by the composition of the sample. DNA sequencing fragments are introduced into the capillary along with other competing negative ions present in the sample solution. The injection process is biased towards faster migrating small ions and shorter DNA fragments. Due to its transient nature, the stacking process is not amenable to quantitative evaluation. The effect of stacking under similar conditions is often irreproducible because it depends on the local condition at the injection point, such as the sample composition, solute chemistry, and the spatial distribution of the applied electric field.

Recently a significant improvement in the stacking procedure was reported by B. Karger's group at Barnett Institute [Salas-Solano 98, Ruiz-Martinez 98]. The researchers instituted a meticulous sample clean-up procedure in which template DNA was thoroughly removed and the total concentration of salts was drastically reduced. In addition, they determined that the injection is more effective at an optimum relatively low electric field of 25 V/cm. As the result of these changes, the injected amount of the sequencing fragments was increased 10–50-fold. This allowed the authors to increase the range of a reliable and reproducible separation to above 1000 bp with a base calling accuracy of 99%.

This remarkable result was achieved with a rigorous cleaning protocol that involved an ultra-filtration through a special membrane treated with linear polyacrylamide (for the template removal) and gel filtration for desalting. This is an expensive and time-consuming process. Moreover, even this greatly amplified stacking is effective only for small volumes of the injected sample. The injection was conducted at the optimum electric field of 25 V/cm, which is about one order of magnitude lower than that commonly used. The duration of injection was optimized at 80 sec, about one order of magnitude longer than that commonly used. Therefore, while the sample is concentrated to a higher degree, the total injected amount remains close to that commonly used. The stacking effect fades away as the length of the injected sample increases. The transient deceleration force influences the motion of a charged fragment only momentarily at the entrance of the capillary. When in the capillary, the fragment is drifting under the injection field with a constant speed, according to its molecular mobility. If the time of drift is long, the effect of stacking is diluted and eventually lost.

Chien and Burgi [Chien 92] reported stacking of very large injected volumes using their field-amplified sample injection method for a free capillary electrophoresis. However, the method is based on the electroosmotic effects and is unsuitable for gel electrophoresis.

To the best of our knowledge, no existing method offers inexpensive, reliable and reproducible in-capillary densification of large volumes of DNA samples. The intent of this proposal is to develop such a method.

Realization of the ESC method will lead to a significant improvement of the gel CE analysis by reducing the cost of operation and equipment and expanding the scope and versatility of CE. Below we present arguments to support this point of view.

Minimizing Waste of the DNA Material in Capillary Electrophoresis

In gel CE, the amount of injected material is delicately balanced between two conflicting interests, resolution and detection. For better detection, one needs larger amounts of material, but this leads to poorer resolution. Indeed, for higher resolution it is desirable to have sample of smaller length. This requirement arises for the following reason. During the electrophoretic separation, DNA molecules aggregate in different zones according to their size. These zones are detected at the output end of the capillary by their fluorescence. Two zones become well resolvable when the separation between their centers exceeds the length of the original injected sample. The separation is proportional to the running time. However, at longer times the resolution is degraded by diffusion processes that smear the peaks of the separated zones. In this trade-off between the separation and diffusion, the optimum compromise is usually found when the spacing between the zones is several hundred microns. This sets the upper limit for the length of the injected sample such that its volume is only on the order of few nanoliters. For a reliable detection, this miniscule volume should contain a sufficient amount of DNA. This implies that the injected sample material is highly concentrated. Such genetic material is expensive and not always available. Sadly, the lion's share of it is routinely wasted. As a practical example, in our standard run-of-the-mill separation a sample is electrokinetically injected during 10 sec from a 2 $\mu$L volume containing the DNA sample (smaller volumes are difficult to handle). We estimate that the injected portion of the DNA material does not exceed several percent from the total amount DNA contained the source tube. If the run is successful, the rest of the DNA sample is discarded.

With the development of the new ESC technique that can compress large volumes of samples to a much smaller volumes, this waste can be minimized. One can inject much larger volumes of low-concentration sample material. The sample preparation routine can be simplified and the cost of the material preparation greatly reduced. This is of a great economic importance for the practical application of the DNA CE. As an illustration, an average fully utilized sequencer working round the clock can carry out twelve runs a day, or about four thousand runs per year. The cost of a standard labeled template 100-run kit from ABI is about $600; the cost of the material used per year is about $24,000, prohibitively high for an average researcher. With our method, this cost will be dramatically reduced.

B.2.2. Cost Reduction of Sequencing Equipment

The ESC method will produce much higher concentrations in the sample material. When the sample is separated into zones, each zone will also be more concentrated. Since the intensity of the excited fluorescence is directly related to the concentration, we expect the fluorescence from the compressed zones to increase. The excess fluorescent power of the compressed sample may be used not only to cut waste, but also to improve the sequencing instrument and reduce its cost. Today a state of the art sequencing instrument employs as an excitation source an Ar laser with the output power of 30–40 mW and a price tag of several thousand dollars. With the implementation of the ESC technique, a simple, lighter and cheaper 1 mW laser will suffice. This will reduce the cost of the sequencing equipment. This will also alleviate the bleaching problem that often plagues the CE analysis.

B.2.3. Significance of the ESC Method for Our Research

For our own research at SUNY SB, the employment of the ESC method will be a pivotal point. We have developed a novel multicolor fluorescent detection technique for the implementation in the DNA sequencing [Gorfinkel 1995]. The technique is based on the illumination of the sample by several different light sources, each with a different wavelength $\lambda_i$ and modulated in time in a distinguishable way. Detection of fluorescence is then performed by a single "color-blind" detector. This is conceptually different from the existing multicolor detection techniques, where the distinct fluorophores are excited by a single light source, but each kind of fluorophore is detected by a separate detector. We have demonstrated that our technique of excitation yields a 10-fold increase in the sensitivity compared with the standard technique.

We have achieved a further dramatic increase in the sensitivity by utilizing a single photon counter as detector of the fluorescent radiation, replacing the standard analog photodetector. We have found that with the single photon detection, the minimum number of photons necessary for a reliable identification of a fluorescent dye can be as low as 100. We were able to reliably detect very small photon fluxes down to $5 \times 10^{-17}$ W. In the course of our research we have developed a Single Photon Detection (SPD) module with an increased dynamic range, 23 bits, which is a more than two order of magnitude improvement compared to currently prevalent 16 bits formate.

Expanding the Range and Versatility of the Gel CE Analysis.

The separation process is a constant battle between the good and the evil—drift and diffusion. The drift process with length-dependent mobility separates the zones and moves them further apart while the diffusion smears the contrast between the separated zone peaks. In this battle, time is against us because the separation distance is a linear function of time while the diffusion length is sublinear in time. One of the ways to minimize the diffusion relative to drift is to shorten the separation time. However, the separation time is directly related to the linear size of the original sample (to be detectable, the zones should be separated by a distance larger than the original sample length). Therefore, for shorter separation times the sample length should be reduced. With the ESC method, we can concentrate an injected sample in a very small volume. We expect that this will dramatically reduce the time required for the separation and, as a result, the extent of the diffusion. With reduced diffusion, DNA fragments of the same molecular weight can be resolved with shorter capillaries. Even more significantly, for the same capillary length we can now resolve longer DNA fragments. This will further expand the range of the separation process.

The method will give both the researcher and the clinician an option to choose their own modus operandi. Compression of larger volumes of low concentration DNA to standard concentrations will reduce the cost of the PCR process as well as DNA waste. Alternative regimes of compressing the samples of standard templates to a higher concentration will reduce the required illumination. The sequencing apparatus can be made lighter and significantly less expensive by using low-power illumination sources. Sequencing regimes can be adjusted to particular research or clinical needs.

The method will add to the DNA analysis a new dimension—versatility. In combination with the novel method of fluorescence detection (modulated multicolor illumination and single photon detection), the method will allow the utilization of light-emitting diodes as the illumination source. A light inexpensive (under $10K) CE analyzer for everyday commercial use with LED-based detection could be put on the desk of every clinician. For very special research-type high-resolution one-of-the-kind equipment, one could use more expensive laser-equipped detection systems.

Description of the Proposed Method and Apparatus

In this section, we shall outline the ESC method for on-line densification of the DNA sample. First, we shall explain the particulars of the method (Sect. D.1.). Then we shall report our preliminary experiments with the reverse field compression with different barrier media (Sect. D.2, D.3). These experiments were carried out on the experimental DNA sequencing instrument designed and built at the SUNY SB Electrical Engineering department as our research tool. In comparison with a commercial instrument, it has a great advantage of flexibility: many experimental parameters such as the length of the capillary, the times and the electric fields of various cycles, etc. can be easily adjusted. In this section we give a brief description of our instrument (Sect. D.4). At the end of this section, we describe our work plan for the development of the compression method (Sect. D.5.).

D.1. How the Method Works

The sample is injected by the standard electrokinetic injection with the notable difference that the length of the injected sample (duration of the injection) is determined only by the concentration of the sample in the cuvette and the desired concentration.

After the injection stage, the process proceeds to the compression stage. The inlet of the capillary is immersed into, or pressed against, a special barrier medium, impenetrable for DNA fragments. The polarity of the electric field is reversed, so that the negatively charged DNA fragments will be driven towards the inlet of the capillary where they will be pressed against the barrier and accumulate there.

We believe the compression in our method will be more effective and reproducible than that in the stacking method. The advantages are owing to the fact that the compressing electric field created by an external power supply will have a well defined value and can be applied during any desired time interval. In contrast, the compressing electric field in the stacking method is transient and uncontrollable. To begin the separation process, the inlet of the capillary is immersed in the buffer cuvette and the applied field is reversed again. The Use of Low Power Sources for Fluorescence Excitation Because of high density of the DNA sample we can proceed with the replacement of the costly multicolor laser based illumination source with an inexpensive miniature LED source. The LED source module comprises a group of LED devices with current drivers and programmable modulation circuits. The output from the module is a four-color beam where each color is modulated at frequencies in the range of 100–300 Hz. The fiberized LED illumination source can be easily incorporated into our sequencing instrument described in the Sect. D.4.

D.2. Barrier Medium

Finding a medium that can use as a block for the DNA molecules is the main goal of our proposed project. What properties do we seek? Firstly, the medium should be a barrier for DNA fragments. Next, it should either be a good conductor itself or be permeable for small ions of the solute and water to provide a good conductance in the capillary system.

A natural realization of the DNA barrier medium is a very concentrated gel. The DNA mobility $\mu$ in gels has a very strong inverse exponential dependence on the average pore size $\alpha$ [Noolandi 93], while the mean pore size $\alpha$ varies inversely with the gel solid concentration C, viz.$\alpha$ $C^{-0.75}$ [Quesada 97]. It is possible to greatly suppress the mobility by increasing the concentration of gel. For example, for polyacrylamide gels, the average pore size was found to vary from 50 nm to less than 1 nm when the solid concentration was increased from 3 to 30% [White 60]. On the other hand, even at their highest concentrations, these materials will behave as reasonable conductors.

Another realization of the DNA barrier is an electrostatic stopper. It can be realized as a fine metal grid positioned at the inlet of the capillary and set at zero potential at the compression cycle. Note that a barrier of the electrostatic type will block all charged particles, independent on their size.

A solid metal electrode can also be used as a barrier. However, such a barrier would not provide any carriers of charge into the solution to compensate the charge of the DNA fragments compressed at the barrier. This means that, in principle, the compression process should be self-limiting. It will stop when the field of the DNA charge screens the applied compressing field. The compression degree at this point depends on the nature of the metal of the barrier and the distribution of charges in the capillary. Our preliminary results (next section) with a solid metal barrier suggest that this line of investigation is definitely worth pursuing.

After the injection, the compression will be performed with different blocking media, for some barriers, we may have to institute an intermediate step between the compression and separation whose purpose will be to dissociate the compressed material from the barrier interface. This step will be carried out without moving the capillary from its position relative to the barrier, by reversing the applied bias to the separation polarity.

After the completion of the compression stage, the capillary will be immersed in the standard buffer and the compressed sample will undergo the electrophoresis. The compressed zones will be observed at the window with our fluorescence detection system. We shall record the temporal length and intensity of the compressed zone F and thus evaluate the size of the compressed zone $d_z$ and the relative amount of injected DNA material. At this stage, we shall be using, as a test DNA material, a set of genetic markers D.3. Preliminary Experiments D.3.1. Experimental Setup and Results The preliminary compression experiments were carried out in our capillary setup (Section D.4). As an electrophoretic agent, we used a mixture of two dyes Xylene Cyanole and Bromophenol Blue (Aldridge Catalog, items 33,594-0 and 11,439-1, respectively). We determined that in a standard polymer separation medium, the electrophoretic mobilities of the two dyes are close to those of DNA fragments with the molecular lengths of about 80–100 bp and 12–20 bp, respectively. The dye mixture has a bright blue color so that its dynamics in the tube can be observed with a naked eye or through a microscope. The dye experiments produced a convincing visual demonstration of the compression effect.

The dye mixture was injected into the capillary at the injection voltage of 16 kV. The duration of the injection was usually 3 min. The current during the injection was about 10 $\mu$A. The length of the injected sample (light blue color) could be observed visually through the stripped capillary walls at the inlet and was about 1 cm. After the injection, the inlet of the capillary was blocked by the barrier and the compression voltage of the same magnitude and duration was applied. After the compression, the sample was examined by eye and under the microscope.

For the blocking medium we prepared a high-density PAA gel (T=30%, C=5%). First, the capillary was inserted into the gel by piercing the gel with the capillary. During the compressing cycle, the reverse current was of about the same magnitude of 10 $\mu$A. After the compression, we observed a blurred blue stain at the end of the channel bored by the capillary in the gel. No compressed material was observed in the capillary.

In the next experiment, the end of the capillary was pressed against the solid surface of the gel. Although the end of the capillary was rugged and the contact was not tight, the current through the system still held at about 10 µA. After the compression, when the capillary was withdrawn, we observed an intensely bright dark blue spot, similar to an ink drop, on the surface of the gel. No dye was left in the capillary.

In still another experiment, we used aluminum foil as a barrier. This time, the current decreased from 10 A at the beginning of the compression down to zero value. The dye was compressed at the inlet of the capillary to a cylinder less than 40 µm in height (under the microscope the height of the compressed dye was about half of the inner diameter of the capillary). No dye was detected on the foil.

D.3.2. Interpretation of Results

The most plausible explanation of the first result is that the dye escaped through defects and microcracks that were formed when the solid gel was pierced by the capillary. We conclude that the immersion should be done before the solidification. In case of PAA gels, the cross-linker should be added after the immersion. Another approach is to use thermo-sensitive gels that change their viscosity with temperature [Wu 98]. After the injection, the immersion should be done when the gel is at its low viscosity state; for the compression the gel should be brought to its high viscosity state.

The second experiment demonstrated that the compression is a reality. The 1 cm long sample was compressed into a virtually two-dimensional spot. In this arrangement, however, the experiment did not work because the dye was left deposited on the surface of the gel barrier. We suspect that it was due to a rugged interface between the capillary and the barrier. Alternative explanation is some binding between the compressed material and the gel. To improve the interface, we intend to institute the protocol of capillary immersion into a liquid gel and subsequent solidification. In addition, we should probably introduce an intermediate step to pull the compressed material from the interface into a capillary by applying a positive voltage for a short time while the capillary is still immersed into a barrier medium.

Result of the third experiment is encouraging. Note that the blocking barrier does not satisfy the second condition of being permeable by the solvent ions. Indeed, not only is the metal foil a barrier for DNA fragments, it is also a barrier for all moieties present in the solution. Therefore, at the compressing polarity it cannot supply a positive charge to compensate the negative charge of compressed material. The compression is self-limiting due to the formation of a space charge at the interface. The space charge formation plays a positive role, because due to its presence the compressed material stays in the capillary and does not adhere to the metal surface.

It is instructive to compare this result with the standard stacking (10 sec injection) of the same dye where the size of the injected zone is about 300 µm. While the compressed zone was almost an order of magnitude shorter (less than 40 µm), the amount of compressed material, however, was roughly 20 times greater (the injection time in the compression experiment was 180 sec vs. 10 sec for the standard process).

Our preliminary dye compression results, though very encouraging, should be taken with caution because they were obtained on the dye mixture whose behavior under the ESC may be quite different from that of DNA. We intend to conduct extensive experiments to verify the ESC technique with a series of extensive experiments carried out on various genetic materials (see Section D.5).

Design and Development of a Programmable Module for Injecting DNA Material into the Capillary In the conventional capillary electrophoresis, one has peculiar problem which arises during electroinjection of the DNA material from a microcentrifuge "sample" tube into the capillary and leads to a significant waste of precious material. The problem is that the amount of material loaded into the sample tube is of necessity too large because it must exist at a relatively high concentration. Lowering of the concentration of labeled material in the tube would lead to longer electroinjection time—which would be usually unacceptable because it would lengthen the initial sample introduced in the capillary and degrade its subsequent separation and sequencing. We have developed a proprietary technique for solving this problem, as illustrated in FIG. 1. The three tubes in FIG. 1 illustrate three stages of capillary electrophoresis (CE). The left and the right tube represent the conventional loading and drive stages, respectively. However, the sample into the capillary in the first stage has lower concentration of DNA fragments, takes longer time to inject, and initially occupies longer stretch of the capillary, compared to samples commonly used in DNA separation by CE. The low-concentration sample is compressed by the negative drive in second stage. The technique is expected to enhance the resolution of CE and at the same time lower the amount of labeled material consumed. Referring to FIG. 1, three-tube electroinjection is shown with the following features: (1) capillary; (2) microcentrifuge tube; (3) labeled DNA sample; (4) "plug" gel of high electrical conductivity but impenetrable for DNA fragments; (5) Buffer TBE/5M; (6) low-concentration DNA sample, initially introduced in the capillary; (7) spatially "compressed" DNA sample; (8) electrophoretic separation of "compressed" sample; (9) positive "loading" voltage; (10) negative "compressing" voltage; (11) positive "separating" voltage. Initially loaded sample (6) is too long to be used for high-quality electrophoretic separation. It becomes adequate after the compression stage.

Figure 2:
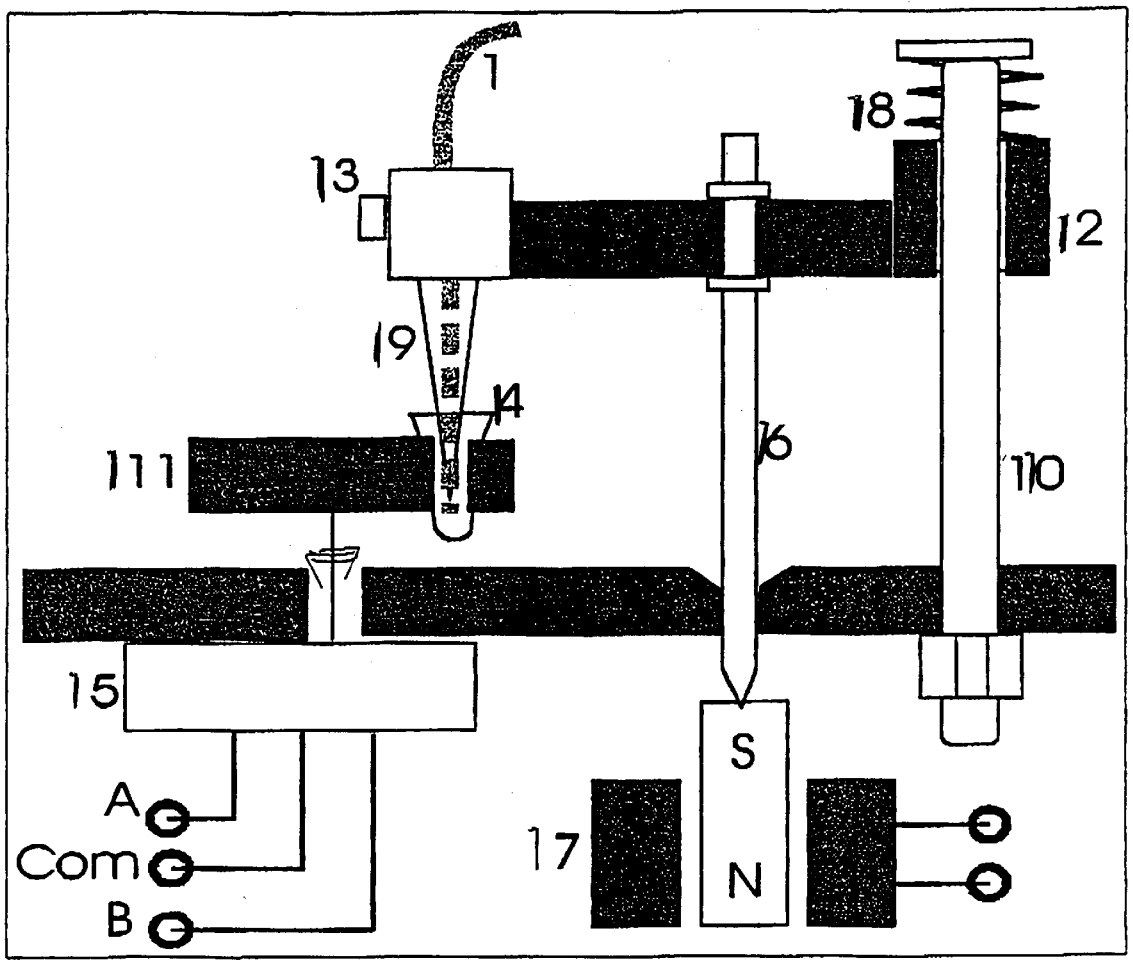
FIG. 2 is a schematic showing an automatic tube changer in accordance with the present invention.

The tube changing procedure will preferably be automated. A design of the automatic apparatus is shown in FIG. 2. Referring to FIG. 2. an automated tube changer is shown with the following features: (1) capillary; (12) capillary fixture holder; (13) capillary fixture; (14) replaceable tube; (15) reversible step motor; (16) drive for holder 12; (17) electromagnet; (18) return motion spring; (19) conical guide with Pt electrode; (110) cylindrical support; (111) rotating holder. The platinum electrode in (19) connects to the high-voltage circuit with reversible polarity.

Design and Development of a Programmable Power Supply for Electrophoresis

The preceding section illustrates the need for a controlled high-voltage power supply (CHVPS), which would permit changing the magnitude and even polarity of the applied voltage in a stable and programmable fashion.

Figure 3:
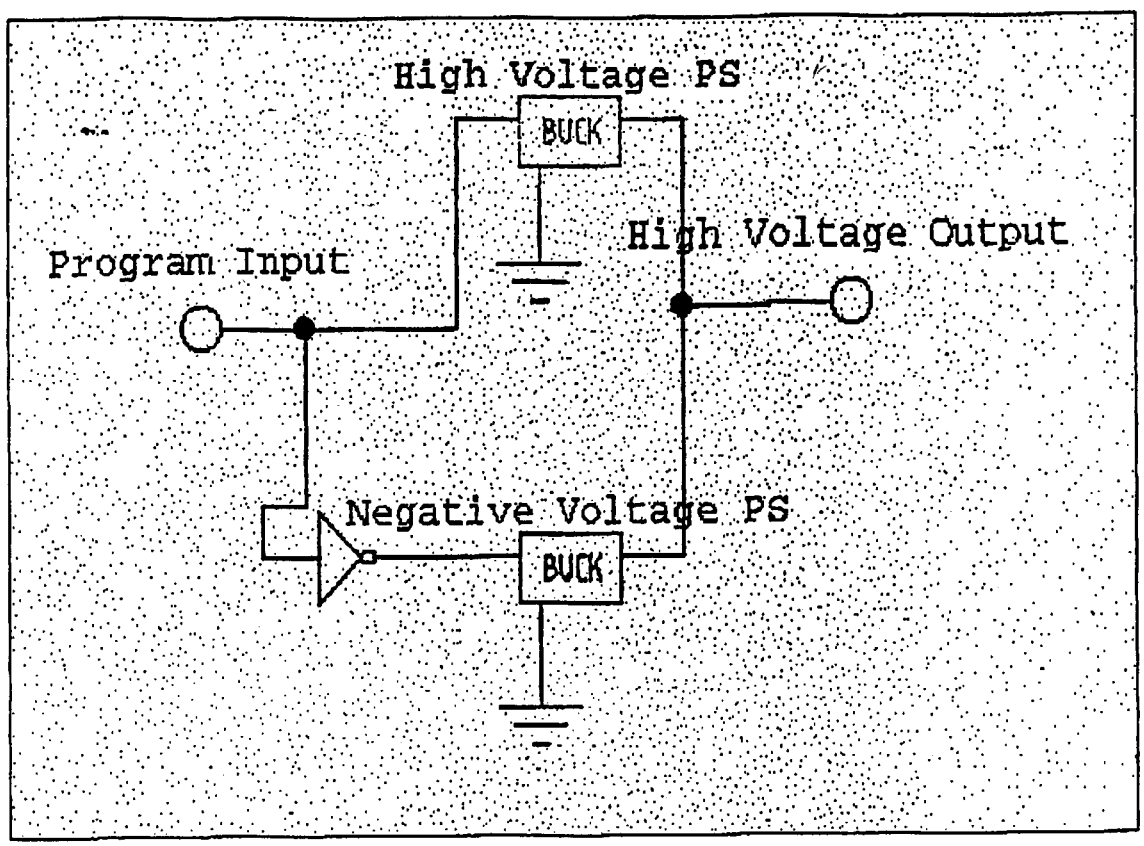
FIG. 3 is a schematic diagram of a programmable high voltage supply for use with the present invention.

The CHVPS will be controlled automatically by the central control system of the apparatus but the operator can assume manual control at any time. Referring to FIG. 3, a programmable high voltage supply is shown for use with the present invention.

The block is assembled on the basis of the universal high voltage unit (EMCO #4150). Control of the electric regime is provided by a built-in current meter and a high-voltage gauge. The CHVPS will be controlled automatically by the central control system of the apparatus but the operator can assume manual control at any time.

Commonly assigned provisional applications U.S. application Ser. No. 60/110,712 and 60/110,714 are incorporated herein by reference.

G. LITERATURE CITED

[Chien 92]: Chien, R. L. and Burgi, D. S., "Sample stacking of an extremely large injection volume in high-performance capillary electrophoresis", *Anal. Chem.* 64, 1046–1050 (1992)

[Gorfinkel 95]: Gorfinkel, V. B. and Luryi, S., "Method and apparatus for identifying fluorophores", U.S. Pat. No. 5,784,157 (filed 1995, issued July 1998)

[Noolandi 92]: Noolandi, J., "Theory of gel electrophoresis", in *Advances in Electrophoresis* V5, A. Crambach, M. J. Dunn, B. J. Radola, Eds. (1992) pp. 2–56 and references therein.

[Quesada 97]: Quesada, M. A., "Replaceable polymers in DNA sequencing by capillary electrophoresis", *Current Opinion in Biotechnology* 8, 82–93 (1997).

[Ruiz-Martinez 98]: Ruiz-Martinez, M. C. et al., "A sample purification method for rugged and high-performance DNA sequencing by capillary electrophoresis using replaceable polymer solutions; A. Development of the cleanup protocol", *Anal. Chem.* 70, 1516–1527 (1998)

[Salas-Solano 98]: Salas-Solano, O.et al., "A sample purification method for rugged and high-performance DNA sequencing by capillary electrophoresis using replaceable polymer solutions; B. Quantitative determination of the role of sample matrix components on sequencing analysis", *Anal. Chem.* 70, 1528–1535 (1998)

[White 60]: White, M. L. "The permeability of an acrylamide polymer gels, *J. Phys. Chem.* 64, 1563–1565 (1960)

[Wolf 95]: Wolf, S. M. and Vouros, P. "Incorporation of the sample stacking techniques into the capillary electrophoresis CF FAB mass-spectrometric analysis of DNA adducts", *Anal. Chem.* 67, 891–900 (1995).

[Wu 98]: Wu, C. et al. "Viscosity-adjustable block copolymers for DNA separation by capillary electrophoresis", *Electrophoresis,* 19, 231–241 (1998).

Having described preferred embodiments of a system and method of the invention (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method of spatial compression of a DNA sample inside a capillary for gel capillary electrophoresis comprising the steps of:

providing a capillary having an inlet end and an outlet end;

providing a first electrode adjacent said capillary inlet end and a second electrode adjacent said capillary outlet end;

electrophoretically injecting DNA sample into said inlet end of said capillary by applying a voltage across said first electrode and said second electrode;

contacting the inlet end of the capillary with DNA barrier material;

compressing the DNA sample against the DNA barrier material by applying a voltage having a polarity reversed to the electrokinetic injection voltage across said first electrode and said second electrode; and electrophoretically separating the compressed DNA sample by applying a voltage having a polarity reversed to the compression voltage.

2. The method of claim 1, wherein the compressed sample occupies about less than 40 $\mu$m.

3. The method of claim 1, wherein the DNA barrier comprises a high-density PAA gel including about 30% T and 5% C.

4. The method of claim 3, further comprising the step of limiting the compression by a space charge at an interface of the aluminum foil, wherein the DNA sample does not adhere to the aluminum foil.

5. The method of claim 1, wherein the DNA barrier comprises an aluminum foil disposed at a lower portion of the capillary.

6. The method of claim 1, wherein an electrophoretically separate sample can be viewed under a single photon detection module.

7. The method of claim 6, wherein the single photon detection module comprises a dynamic range of about 23 bits.

8. The method of claim 6, wherein down to about 100 photons can be used for identification of a fluorescent dye in the DNA sample.

9. The method of claim 6, wherein the single photon module further comprises a four-color beam wherein each color is modulated at a frequency range of about between 100 and 300 Hz.

10. The method of claim 1 wherein the step of electrokinetically injecting the DNA sample is performed at a voltage of about 16 kV and current of about 10 $\mu$A for about 180 seconds.

11. The method of claim 1 wherein the step of electrokinetically injecting the DNA a sample is performed at a voltage less than about 20 kV and current less than about 10 $\mu$A.

* * * * *